United States Patent [19]

Meyers et al.

[11] Patent Number: 6,110,663
[45] Date of Patent: Aug. 29, 2000

[54] METHODS FOR DETECTING, TITERING, AND DETERMINING SUSCEPTIBILITY TO PAPILLOMAVIRUS

[75] Inventors: Craig M. Meyers, Hummelstown, Pa.; Michelle A. Ozbun, Albuquerque, N. Mex.

[73] Assignee: The Penn State Research Foundation, University Park, Pa.

[21] Appl. No.: 09/190,433

[22] Filed: Nov. 12, 1998

[51] Int. Cl.$^7$ .......................... C12G 1/70; G01N 33/567; C12P 21/04; C12N 15/00

[52] U.S. Cl. ............................ 435/5; 435/7.21; 435/69.8; 435/7.9; 435/320.1; 435/235.1

[58] Field of Search .............................. 435/5, 7.21, 69.8, 435/7.9, 235.1, 320.1

[56] References Cited

U.S. PATENT DOCUMENTS

| | | | |
|---|---|---|---|
| 4,983,728 | 1/1991 | Herzog et al. | 435/5 |
| 5,364,758 | 11/1994 | Meijer et al. | 435/5 |
| 5,484,699 | 1/1996 | Bouma et al. | 435/5 |
| 5,770,384 | 6/1998 | Androphy et al. | 435/7.8 |

OTHER PUBLICATIONS

Thierry, F., et al. (1990) "Cooperative activation of transcription by bovine papillomavirus type 1 E2 can occur over a large distance." Mol. Cell. Biol. 10: 4431–4437.

Thierry, F. and M. Yaniv. (1987) "The BPV1–E2 trans–acting protein can be either an activator of a repressor of the HPV 18 regulatory region." EMBO J., 6: 3391–3397.

Ushikai, M., et al. (1994) "Trans activation by the full–length E2 proteins of human papillomavirus type 16 and bovine papillomavirus type1 in vitro and in vivo: cooperation with activation domains of cellular transcription factors." J. Virol. 68: 6655–6666.

Ustav, M. and A. Stenlund. (1991) "Transient replication of BPV–1 requires two viral polypeptides encoded by the E1 and E2 open reading frames." EMBO J. 10: 449–457.

Wasylyk, B., et al. (1984) "A novel eukaryotic promoter element: the simian virus 40 72 base pair repeat." Fed. Proc. 43 (2): 226–234.

Zhou, J., et al. (1995) "Early phase in the infection of cultured cells with papillomavirus virions." Virology. 214: 167–176.

Zur Hausen, H. and A. Schneider. (1987) "The role of papillomaviruses in human anogenital cancer." The Papovaviridae, vol. 2: The papillomaviruses. Plenum Press, New York.

Androphy, E.J. et al. (1987) "Bovine papillomavirus E2 trans–activating gene product binds to specific sites in papillomavirus DNA". Nature (London). 325: 70–73.

Angell et al. (1992) "An in vitro system for studying the initial stages of cottontail rabbit papillomavirus infection." J. Virol. Meth. 39: 207–216.

Berg, M. and A. Stenlund. (1997) "Functional interactions between papillomavirus E1 and E2 proteins." J. Virol. 71: 3853–8363.

Bouvard, V.A. et al. (1994) "Characterization of the human papillomavirus E2 protein: evidence of trans–activation and trans–repression in cervical keratinocytes." EMBO J. 13: 5451–5459.

Butel, J.S. et al. (1972) "Studies with human papillomavirus modeled after known papovavirus systems." J. Natl. Cancer Inst. 48: 285–299.

Christensen, N.D. and J.W. Kreider. (1990) "Antibody–mediated neutralization in vivo of infectious papillomaviruses." J. Virol. 64: 3151–3156.

Del Vecchio, A.M. et al. (1992) "Transient replication of human papillomavirus DNAs." J. Virol. 66: 5949–5958.

Dvoretzky, R.S. et al. (1980) "A quantative in vitro focus assay for bovine papilloma virus." Virol. 103: 369–375.

Hawley–Nelson, P. et al. (1988) "The specific DNA recognition sequence of the bovine papillomavirus E2 protein is an E2 dependent enhancer." EMBO J. 7: 525–531.

Hirochika, H. et al. (1987) "Enhancers and trans–acting E2 transcriptional factors of papillomaviruses." J. Virol. 61: 2599–2606.

Kovelman, R. et al. (1996) "Enahanced transcriptional activation by E2 proteins from the oncogenic human papillomaviruses." J. Virol. 70: 7549–7560.

Lambert, P.F. (1991) "Papillomavirus DNA replication (mini–review)." J. Virol. 65: 3117–3420.

Lancaster, W.D. and W. Meinke.(1975) "Persistence of viral DNA in human cell cultures infected with human papillomavirus." Nature (London). 256: 434–436.

Lancaster, W.D. and C. Olson. (1982) "Animal Papillomaviruses." Microbiol. Rev. 46: 191–207.

Meyers, C.M. (1996) "Organotypic (raft) epithelial tissue culture system for the differentiation dependent replication of papillomavirus." Meth. in Cell Sci. 18: 201–210.

Meyers, C.M., et al. (1992) "Biosynthesis of human papillomavirus from a continuous cell line upon epithelial differentiation." Science. 257: 971–973.

Meyers, C.M., et al. (1994) "Tissue culture techniques for the study of human papillomaviruses in stratified epithelia." A Laboratory Handbook. Academic Press, Inc.

Meyers, C. M., et al. (1997) "Synthesis of infectious human papillomavirus type 18 in differentiating epithelium transfected with viral DNA." J. Virol. 71: 7381–7386.

Moskaluk, C. and D. Bastia. (1987) "DNA bending is induced in an enhancer by the DNA–binding domain of the bovine papillomavirus E2 protein." Proc. Natl. Acad. Sci. 85: 1826–1830.

Ozbun, M.A. and C.M. Meyers. (1996) "Transforming growth factor β1 induces differentiation in human papillomavirus–positive keratinocytes." J. Virol. 70: 5437–5446.

Pfister, H. (1984) "Biology and biochemistry of papillomaviruses." Rev. Physiol. Biochem. Pharmacol. 99: 111–181.

Roizman, B. (1990) "Multiplication of viruses: an overview." Virology: Second Edition. Raven Press, New York. pp. 87–94.

(List continued on next page.)

*Primary Examiner*—Ali Salimi
*Attorney, Agent, or Firm*—Thomas J. Monahan

[57] ABSTRACT

Expression vectors that include reporter genes and an operable regulatory region containing a promoter and E2 binding sites of papillomavirus (PV), are used to detect and/or titer papillomavirus by quantitative or qualitative methods.

7 Claims, 5 Drawing Sheets

OTHER PUBLICATIONS

Smith, L.H., et al. (1993) "In vitro HPV–11 infection of human foreskin." Journal of Investigative Dermatology. 10: 438–444.

Smith, L.H., et al. (1995) "Titration of HPV–11 infectivity and antibody neutralization can be measured in vitro." Journal of Investigative Dermatology. 105: 438–444.

Spalholz, B.A., et al. (1988) "Evidence for cooperativity between E2 binding sites in E2 trans–regulation of bovine papillomavirus type 1." J. Virol. 62: 3143–3150.

Steinberg, B.M., et al. (1989) "Tissue site–specific enhancer function of the upstream regulatory region of human papillomavirus type 11 in cultured keratinocytes." J. Virol. 63: 957–960.

Sverdrup, F. and S.A. Kahn. (1995) "Two E2 binding sites alone are sufficient to function as the minimal origin of replication of human papillomavirus type 18 DNA." J. Virol. 69: 1319–1323.

METHODS FOR DETECTING, TITERING, AND DETERMINING SUSCEPTIBILITY TO PAPILLOMAVIRUS

FEDERALLY SPONSORED RESEARCH OR DEVELOPMENT

The U.S. Government may have rights to the invention based on partial support provided through NCI CA-66316 and CA-64624.

FIELD OF THE INVENTION

Expression vectors that include reporter genes and an operable regulatory region containing a promoter and E2 binding sites of papillomavirus (PV), are used to detect and/or titer papillomavirus by quantitative or qualitative methods.

BACKGROUND OF THE INVENTION

Papillomaviruses (PVs) cause benign and malignant tumors in the skin and mucosa. Certain types of human papillomaviruses (HPVs) are associated with human cancers, that is, they are associated with malignant conversion. These include malignancies progressing from respiratory papillomas, skin cancers in patients with epidermodysplasia verruciformis, and anogenital carcinomas, specifically cervical cancers. Cancer of the cervix is reported to be the most common cancer in developing countries and the second most common in women worldwide. Papillomaviruses are associated with greater than 90% of all cases of cervical cancers.

Although papillomaviruses (PVs) are implicated in the etiology of cancers, the complete story of their involvement is not yet known. PVs display remarkable species specificity and strong cellular tropism, and produce both benign and malignant tumors in their natural hosts (Howley, 1996; Lancaster et al., 1982; Pfister, 1987). For example, HPVs have a tropism for squamous epithelial cells and infect only surface epithelia of cutaneous and mucous membranes (Broker and Botchan, 1986; zur Hausen and Schneider, 1987). Although PVs are epitheliotropic, they also show remarkable tissue specificity. Papillomas (warts) have been detected based upon their histological characteristics at numerous sites in humans, including the skin, genital tract, respiratory tract, and oral cavity (Rowson and Mahy, 1967). To date over 75 types of HPVs have been defined based upon their sequence homology (Myers et al., 1996).

Malignant conversion occurs only with infection by some types of HPVs. There are low-risk viruses that are only occasionally associated with cancer. The high-risk viruses commonly associated with malignant conversion include those involved in epidermodysplasia verruciformis and a subset of HPV types that infect the anogenital region.

A virus's host range and cellular tropisms are major determinants of whether or not the outcome of infection is malignant conversion. The restrictions on what type of cells support the replication of a given virus may be dictated at a number of early events in viral infection, including attachment, penetration, uncoating, early gene expression and vegetative viral DNA replication (Roizman, 1990). Some studies have reported that PV virus-like particles can attach to and penetrate a wide variety of cells, suggesting that these cells are susceptible to the virus. However, whether these cells are permissive for replication of PVs has not generally been addressed.

Because PVs show a strong tropism for epithelial cells, host range and tissue tropism (permissiveness) would appear to be determined at a point(s) following attachment and penetration. Because PV virus-like particles can attach and penetrate a wide variety of cells, but only a very narrow range of cell types are permissive for HPV, this suggests that tropism is not a function of attachment and penetration, but rather is an event which follows. Steinberg et al. (1989) provided evidence that control over replication is exerted at the transcriptional level. It appears that blocks in permissivity are exhibited at different viral stages in host epithelial cells versus non-host cell types. Further information on this question would be helpful in understanding and counteracting viral effects. To date, there have been only few reports employing infectious HPV virions that address the molecular mechanisms controlling host range and tissue tropism.

Also, little is known about the differentiation-dependent life cycle of HPVs or how to treat/prevent human papillomatosis. For the majority of HPV types there is currently no efficient in vitro assay for infectivity. Therefore, the study of the basic biology of the virus, especially the assessment of the early phases of infection and investigations of the mechanisms by which HPVs show a strict host range restriction and strong tropism for squamous epithelial cells, is severely limited.

In order to define the determinants of cell/tissue tropism and host range, it is desirable to have a PV infectivity assay. For example, HPVs are dependent upon the state of cellular differentiation to complete the viral life cycle, and the viruses do not appear to display lytic properties. Thus, it is not feasible to develop an in vitro infectivity system based upon the final stages of the life cycle (e.g., a plaque assay or an assay for viral particles). Although mouse C127 cells can be used in focus forming assays for BPV1 and BPV2 virus infection, neither HPV from a plantar wart nor cottontail rabbit papillomavirus (CRPV) were able to induce C127 foci (Dvoretzky et aL, 1983). New methods are needed to assess early phase infections.

The E2 gene product is necessary for the replication and episomal maintenance of viral genomes (Del Vecchio et al, 1992; Ustav and Stenlund, 1991). Thus, E2 expression is required soon after infection to replicate the viral genome copy number to the basal number of 50–200 copies per cell (Broker and Botchan, 1986; Lambert, 1991, Ustav and Stenlurid, 1991). E2 is an important viral transcriptional regulator, facilitated by binding as a dimer to the conserved palindromic sequence $ACCGN_4CGGT$ SEQ ID NO:1, known as an E2 binding site (E2BS) (Androphy et al, 1987; Hawley-Nelson et al., 1988; Moskaluk and Bastia, 1987). In addition, E2 proteins can transactivate heterologous promoters containing several E2BSs located upstream or downstream of the promoters (Spalholz et al., 1988; Thierry et al., 1990). Because the E2 BS sequences are highly conserved among PVs (Myers et al., 1996), a single E2BS assay system potentially could be useful for the analysis of multiple classes of PVs. E2 binding sites are reported to be in different arrangements for cutaneous compared to mucosal lesions. (Garrido-Guerrero et al., 1996).

Nucleotide sequences are reported as probes for the presence and type of papillomavirus (Bouma et al., 1996; Meijer et al., 1994; Herzog et al., 1991). However direct assays that can not only detect the presence of PVs but titer the number of infectious particles, are needed. Comparisons of susceptiblity of different cell types and stages would benefit prevention and therapeutic regimes.

SUMMARY OF THE INVENTION

A method is presented for detecting cells, generally in a tissue sample, that are infected with papillomavirus. The cells do not have to be producing virus to be detected, therefore, the method is useful for early events of viral attacks. The method for detecting papillomaviruses at an early stage of infection includes the following steps: transfecting a cell with an expression vector that includes a reporter gene, and detecting expression of the reporter gene. The tissue sample is transfected with the expression vector directly, or transfected after the tissue cells are cultured in medium. The expression vector also contains one or more papillomavirus E2-binding sites for the early expression E2 protein and the reporter gene is driven by (operably linked to) a suitable promoter. The presence of the papillomavirus in a cell is inferred from the presence or absence of the expression of the reporter gene. Suitable reporter genes include a gene encoding a surface protein or a marker used in fluorescent activated cell sorters (FACS) such as a β-galactosidase. Reporter or marker gene products are detected by quantitative or qualitative means.

A method for determining the susceptibility of a cell to papillomavirus infections includes the following steps: transfecting the cell with an expression vector and detecting the expression of the reporter gene. The expression vector preferably contains at least one E2-binding site and a reporter gene driven by a promoter. The number of E2-binding sites may be 6, 8 or even 12. The susceptibility of the cell to the papillomaviruses is determined from detecting the expression of the reporter gene and/or quantitating the level of expression of the reporter gene. Each cell that is infected will express the reporter gene. The more cells that are infected, the higher the level of reporter gene expression. Also, with some reporter genes, individual cells can provide the information.

A method for titering papillomavirus (determining the number of infectious particles) includes the following steps: obtaining a population of cells that are known to be susceptible and permissive to papillomaviruses; transiently or stably transfecting these cells with an expression vector which contains one or more E2-binding sites and a promoter driven reporter gene; contacting the transfected cells with a standard or test sample of papillomavirus; and quantifying the expression of the reporter gene. The quantity of the papillomaviruses is inferred from, or correlated with, the level of expression of the reporter gene, or is directly inferred by counting individual cells that show expression.

The success of the methods for detecting PV, determining their permissibility, and titering the papillomaviruses, depends on the construction of an expression vector that is responsive to an E2 protein of the papillomaviruses. The expression vector includes the following components: at least one E2-binding site and a reporter gene driven by a promoter, i.e., operably linked to a suitable promoter.

An aspect of the invention is a kit for detecting a papillomavirus. The kit includes the following components: an expression vector containing at least one E2-binding sites and a reporter gene driven by a promoter; and reagents for detecting the expression of the reporter gene.

An aspect of the invention is a kit for determining the susceptibility of cells to papillomaviruses. The kit includes the following components: an expression vector that includes one or more E2-binding sites and a reporter gene driven by a promoter, and reagents for detecting the expression of the reporter gene.

An aspect of the invention is a kit for titering papillomaviruses. The kit includes the following components: cells comprising an expression vector containing one or more E2-binding sites and a promoter driven reporter gene, and reagents for detecting the expression of the reporter gene.

Any expression of the reporter gene detects infection by a PV. Quantitation of a reporter gene expression compared between cell lines/type determines susceptibility of a particular cell type and/or is used to titer the papillomavirus. Kits may contain cells from a cell line stably transfected with the reporter gene construct. Correlation of the level of reporter gene expression with the number of viral particles used for the infection (and/or a specific quantitation of the actual numbers of infected cells) provides quantitative information for comparing susceptibility and for titering.

BRIEF DESCRIPTION OF THE DRAWINGS

FIGS. 3A–D show, pGL2-promoter cores containing zero, two, four, and six E2BS, respectively. E2BSs (stippled boxes) were cloned upstream of the SV40 minimal promoter (SV40-Pr; closed black circles) and the luciferase gene ("lucif"; cross-hatched boxes). FIGS. 3E–H show, constructs that were cloned from the constricts of A–D (respectively) by removing the HindIII-SalI fragment containing the luciferase ORFs and replacing them with the XhoI-SalI fragment containing the β-galactosidase ("β gal"; stippled boxes) ORF from pCMVβ. (MacGregor and Caskey, 1989).

FIG. 4 shows transcriptional activation of E2BSs by endogenous (physiological) levels of HPV31bE2 proteins in the latently HPV31b infected CIN-612 9E monolayer cells.

DESCRIPTION OF THE PREFERRED EMBODIMENT

The present invention provides methods to detect, titer and to determine the relative efficiencies with which HPVs are able to infect cells of different origins (tissues and host species). This information will provide an important basis for investigation of the determinants of host range and cellular tropism, and provides tests for the efficiency of therapeutics or the production of neutralizing antibodies for a vaccine.

HPV infection is detected and quantitated by assaying for the nascent expression of the early protein E2. The assay requires a reporter vector responsive to E2 expression. The reporter is a gene that encodes a protein whose expression can be easily detected and quantified. Thus, the reporter may encode a membrane protein or other proteins and enzymes.

Two sets of reporter gene constructs were made; both contain E2-responsive elements, or E2 binding sites (E2BSs) upstream of a minimal SV40 promoter, (that is, a regulatory region containing elements for efficient and accurate in vivo initiation of transcription). (Wasylyk et al., 1984). In one set of constructs, the E2BSs drive expression of the luciferase reporter gene; in the second, the E2BSs drive the expression of the β-galactosidase ("β-gal") gene. Suitable reporter genes include:

β-galactosidase;
luciferase from
  firefly,
  beetle,
  Renilla;
GFP;
CAT;
any protein that can be detected by antibodies using immunohistological staining or FACS;
any enzyme or substrate that is involved in a reaction where the final product is a dye;
any enzyme or substrate that is involved in a reaction where the final product is a fluoroscein;
any product that provides resistance to a drug or other compound.

Figure 1:
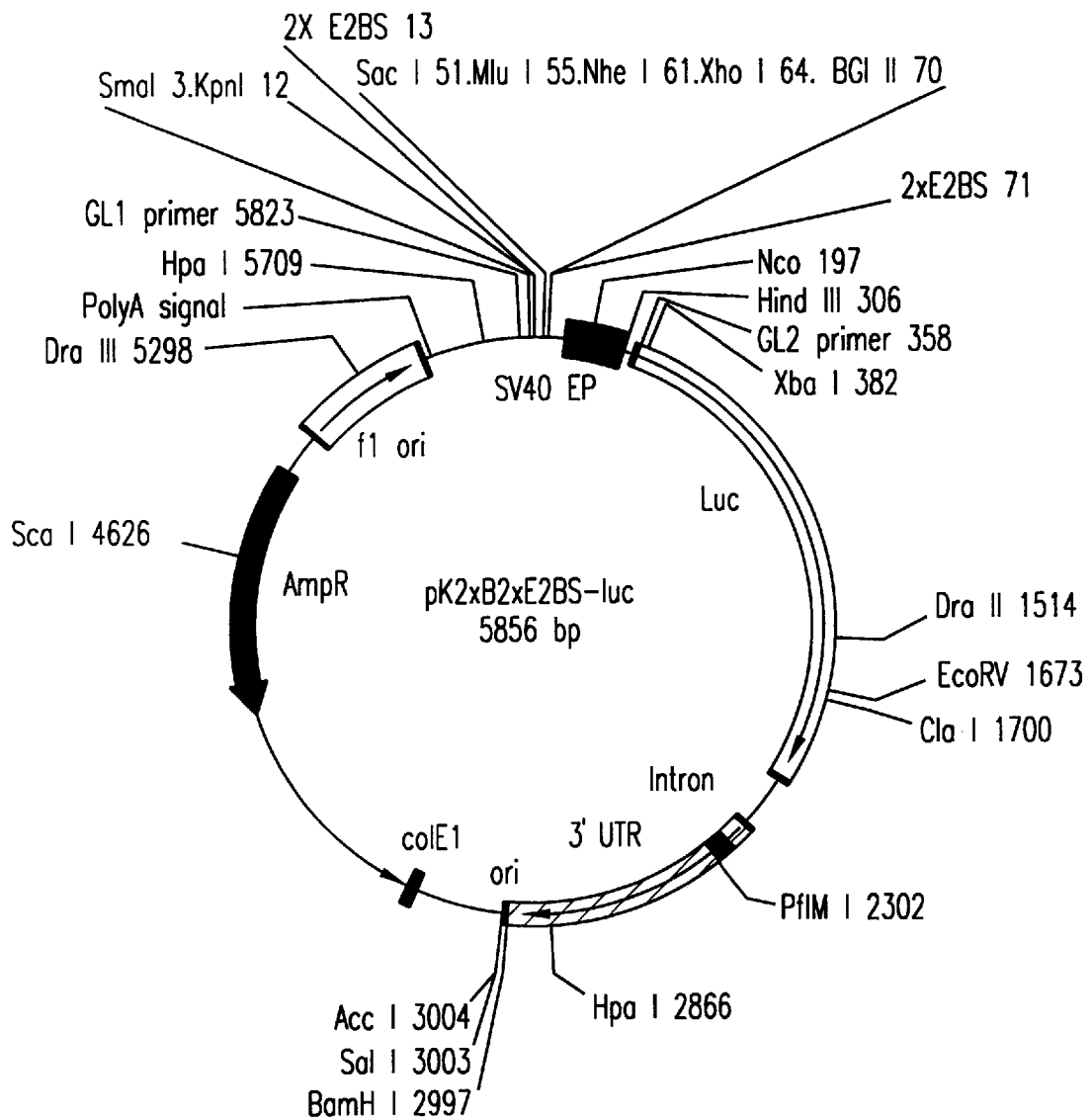
FIG. 1 shows a map of a plasmid named pK2xB2xE2BS-luc and including 5856 bp. Other designations for the plasmid are PP#107-clone #A9; M98-01. There is one copy of oligonucleotide (5'K-CA CCG AAA ACG GTT CAA CCG AAA ACG GTT GTA C-3') SEQ ID NO:2 at the Kpnl site of the pGL2-promoter. There is a copy of oligonucleotide (5'AT CCA CCG AAA ACG GTT CAA CCG AAA ACG GTT A-3') SEQ ID NO:3 at the Bgl II site.

FIG. 1 shows a pE2BS-luc construct. This is an expression vector for luciferase controlled by the SV40 minimal promoter and E binding sites. The construct is responsive to the expression of papillomavirus (PV) E2 protein which binds to the E2BS enhancers and drives expression of the luciferase proteins. pE2BS-luciferase constructs were reported by Kovelman et al., 1996

Other constructs, each differing by the number and placement of the E2 binding sites upstream of the promoter, are all similar in structure and are suitable for practice of the invention, as are other similar constructs not specifically set forth.

The genetic construct (plasmid) is transfected preferably into epithelial cells. When the cells are infected with PV, the virus expresses E2 protein. The expression of the E2 protein activates the expression of luciferase from the plasmid. Upon the addition of a suitable substrate, luciferase produces light. This light is quantitated to determine the number of cells infected by the PV.

Figure 2:
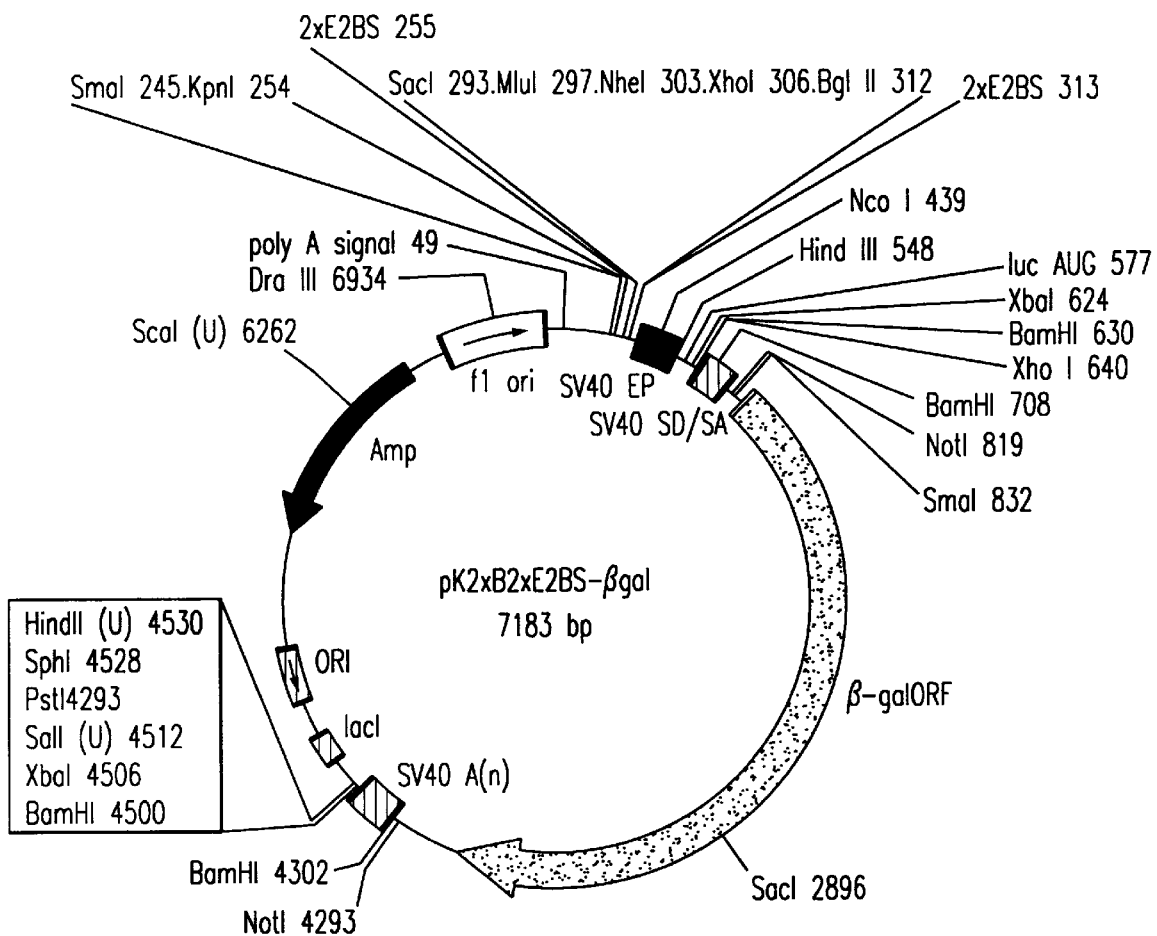
FIG. 2 shows a map of a plasmid named pK2xB2xE2BS-βgal and including 7183 bp. Another designation for the plasmid is M98-05. The expression vector for β-galactosidase driven by the SV40 minimal promoter and four E2 binding sites (BS) (2 sets of 2 BS separated by ≈20 bp.) ScaI-XbaI from pK2xB2xE2BS-luc is put into ScaI-XbaI partial from pCMVβ.
Figure 3:
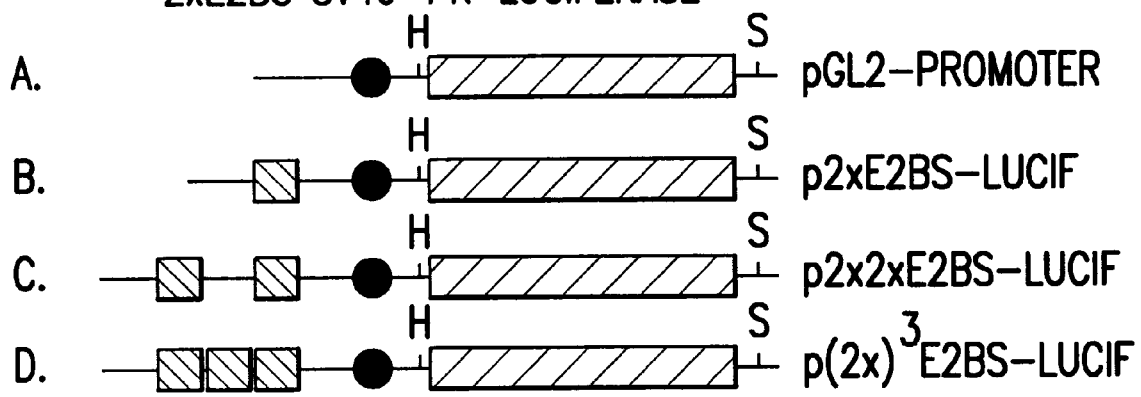
FIG. 3 is a schematic representation of E2BS reporter constructs. Sal I (S), Xho I (X), and Hind III (H) restriction sites are indicated.
Figure 3:
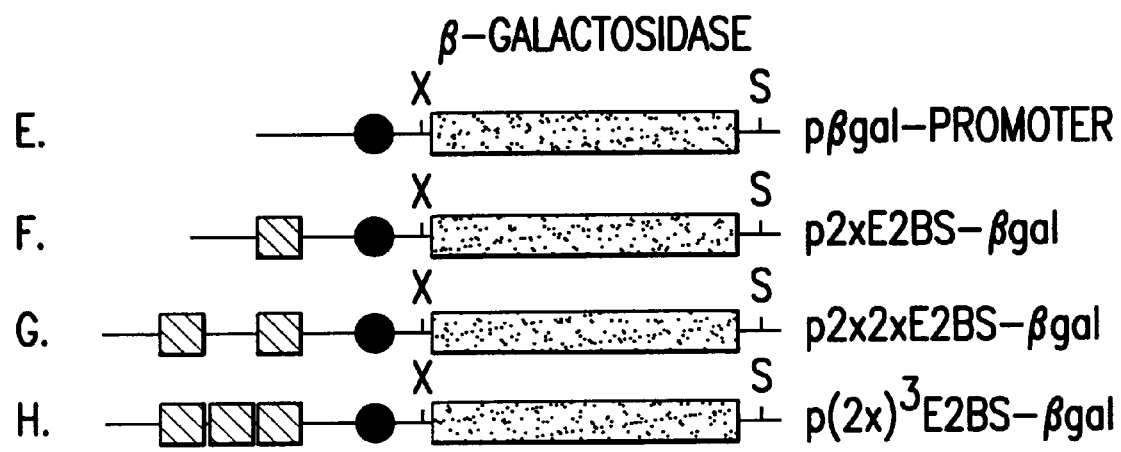

FIG. 2 shows a novel pE2BS-βgal construct. This is an expression vector for β-galactosidase controlled by the SV40 minimal promoter and E2 binding sites. The construct is responsive to the expression of papillomavirus (PV) E2 protein which binds to the E2BS enhancers and drives expression of the β-galactosidase proteins.

A plasmid of the present invention is preferably transfected into epithelial cells. Other cells, while not the most feasible or useful, may also be transfected if there is a proper receptor on the cells. When the cells are infected with a PV, the virus expresses E2 protein. The expression of the E2 protein activates expression of a reporter gene e.g. β-galactosidase, from the plasmid. Upon the addition of a substrate, β-galactosidase produces a blue color in the cells. The blue cells are counted to determine the number of cells infected by the PV.

The luciferase system has the advantage of being sensitive and easily quantitated for light emission using either a luminometer or a scintillation counter. These aspects permit a relative determination of the efficiency of HPV infection. Activation of the E2BS-reporter gene is used in mock infected cells to normalize basal levels. Because the luciferase assay relies upon analysis of cell extracts, it is possible to determine the relative number of cells which are infected.

The β-gal system has the advantage that the infected monolayers can be fixed and stained directly for β-gal activity (MacGregor and Caskey, 1991); individual cells staining blue are indicative of E2 expression resulting from HPV infection. The β-gal assay allows direct calculation of cell percentages infected and of particle-to-infectious-unit ratios, an in vitro assay never before reported for HPVs.

MATERIALS AND METHODS

Cell lines and transfections

The SCC-13 cell line is a human keratinocyte line established from a squamous cell carcinoma of the facial epidermis (Rheinwald and Beckeft, 1981), and the cells are permissive for the HPV life cycle in a raft system developed by Meyers. Furthermore, SCC-13 monolayers can be infected by CRPV. Susceptibility and permissiveness for PV infection make the SCC-13 cell line an attractive candidate for use in establishing efficient infection conditions for HPV. In addition, SCC-13 is an immortalized cell line, and can be more easily manipulated than primary keratinocytes in vitro. The efficiency of HPV infection may differ among cell lines, therefore, the infection conditions established for SCC-13 cells may be verified in other cell lines.

The reporter assay system can be utilized in two ways; the cells will either stably ortransiently express the reporter gene constructs. HPV infection of stably transfected cell lines is preferred and is performed to minimize experimental variables. SCC-13 cells are electropormted with reporter constructs and a selectable marker (e.g., hygromycin B resistance) (Meyers et al., 1997). The efficiency of gene transfer in SCC-13 cells using electroporation is about 50% of viable cells assayed at 48 h. The cells are then exposed to 50 μg per ml of hygromycin B in 10% fetal call serum-E medium for three days. The medium is then replaced with medium lacking hygromycin B. Selecting stably-transfected cell lines has advantages of ensuring that essentially every cell in the population contains the reporter construct and that the times for assaying the infection (expression of E2 protein) can be investigated in intervals from hours to days.

Cloning of E2BS-luciferase reporter constructs

The luciferase reporter system has been shown to be sensitive for the detection of E2 transactivation of E2BSs linked to a minimal SV40 promoter-driven luciferase gene (Kovelman et al., 1996). Multiple E2BSs provide a cooperative effect on the expression of a reporter gene from a heterologous promoter (Spalholz et al., 1988; Thierry et al., 1990). Oligonucleotides were synthesized (Operon Technologies) so that after annealing, a following double-stranded DNA fragment containing two E2BSs with Kpn I- and Bgl II-compatible ends resulted.

The double-stranded region corresponds to the consensus E2BS found in the HPV6 URR (Myers et al., 1996). Luciferase reporter genes were designed to have one, two or three copies of the double stranded oligonucleotide cloned into pGL2-promoter (Promega Corp.). p2xE2BS-lucif was created by ligating a single copy of this DNA fragment into pGL2-promoter digested with Kpn I and Bgl II. P(2x) $^3$E2BS-lucif was created in the same manner, but contains three copies of the double-stranded DNA fragment; the second copy is inverted relative to the other two. P2x2xE2BS-lucif contains two copies of the double-stranded DNA fragment separated by the polylinker sequences between the Kpn I and Bgl II sites of the pGL2-promoter, resulting in a 35-bp spacing between the end of the second E2BS and the start of the third E2BS.

Confirmation of E2BS-luciferase constructs with physiological levels of E2 proteins Numerous studies have investigated the activation of transfected E2BS-reporter constructs by co-transfecting E2 expressing plasmids [Bouvard et al., 1994; Hirochika et al., 1987; Kovelman et al., 1996; Spalholz et al., 1988; Thierry et al., 1990; Thierry and Yaniv 1987; Ustav et al., 1991] However, the high levels of E2 proteins expressed in these systems likely do not reflect physiological levels of PV E2 proteins in infected cells. Thus, it was essential to verify that the E2BS-luciferase constructs could be activated to detectable levels using physiological levels of E2 protein. To address this, the latently HPV31b infected CIN-612 9E cell line was electroporated with increasing concentrations of either pGL2-promoter or p(2x)$^3$E2BS-lucif. (FIG. 4A and B) [Electroporation was found to be the most efficient means of transfecting epithelial cells]. As a control for transfection efficiency, CIN-612 9 E cells were electroporated with increasing amounts of CMV enhancer-promoter driven β-galactosidase plasmid, pCMVβ (MacGregor and Caskey et al., 1989; 1991). Staining for β-galactosidase activity indicated the transfection efficiency of CIN-612 9E cells to be ≈25%.

Figure 4A:
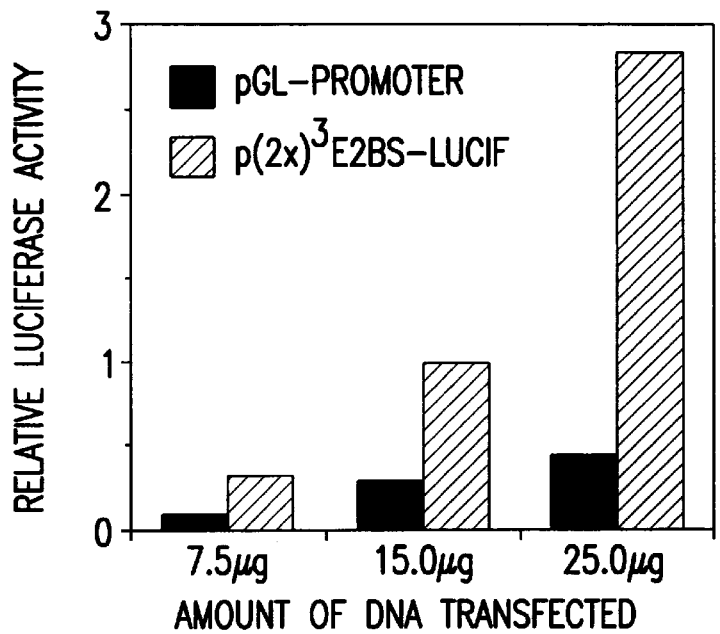
FIG. 4A shows the amount of DNA transfected versus relative luciferase activity.
Figure 4B:
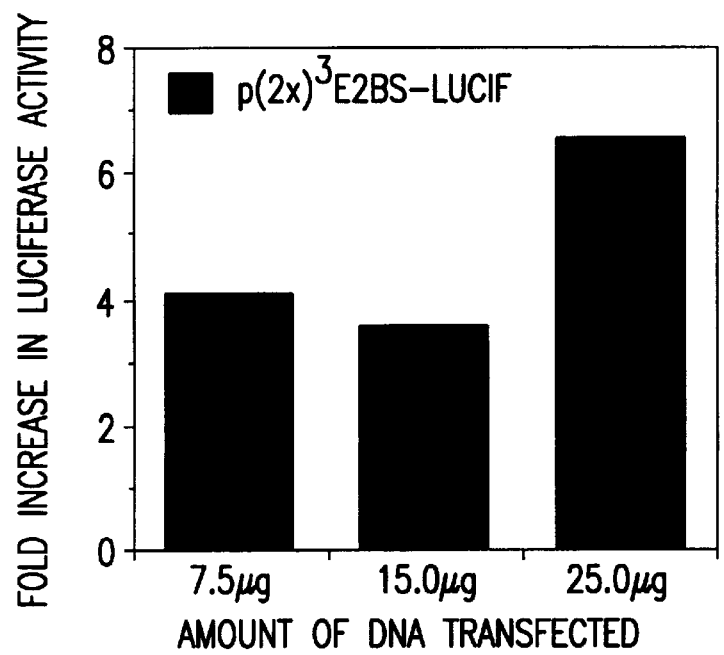
FIG. 4B shows the amount of DNA transfected versus fold increase in luciferase activity.

To reiterate in more detail, transcriptional activation of E2BSs was determined by endogenous (physiological) levels of HPV 31b E2 proteins in the latently HPV31b infected CIN-612 9F monolayer cells. Cells ($5\times10^6$) were incubated with 7.5, 15.0, 25.0 μg of the indicated luciferase constructs; sheared, denatured salmon sperm DNA was used as a carrier by adjusting the total DNA amount to 50 μg. Electroporation conditions were 950 μFa and 0.22 volts; the cells were allowed to recover for 10 min at room temperature (Meyers et al., 1997). Electroporation results in moderate levels of cell death, so it is difficult to determine seeding density. The transfected cells were seeded into triplicate 100 mm cell culture dishes containing mitomycin C-treated J2 fibroblasts in E medium with 10% fetal calf serum. At 48 h post transfection (p.t.), the cells were lysed and assayed for luciferase activity using the Luciferase Assay Reagent, according to the manufacturer's directions (Promega). Values represent the averages of three counts each of 2–3 separate assays performed in 100 mm tissue culture dishes. FIG. 4A shows relative luciferase activity in cells transfected with increasing amounts of pGL2-promoter (no E2BSs; stippled bars) or p(2x)$^3$E2BS-lucif (6 E2BSs; striped bars). FIG. 4B shows fold increase in luciferase activity with increasing amounts of p(2x)$^3$E2BS-lucif over pGL-promoter. Values for p(2x)$^3$EBS-lucif were normalized by dividing by the values of pGL2-promoter for each DNA amount in panel A.

Estimation of transfection efficiency in CIN-612 9E cells electroporated with 25 μg of pCMVβ was determined by assaying for β-galactosidase activity. At 48 h p.t. the cells were fixed with gluteraldehyde, rinsed 3x with PBS and stained as shown by MacGregor and Caskey, 1991. The efficiency of transfection was estimated as a ratio of the numbers of blue staining epithelial cells to the number of total epithelial cells in a given field of view and was estimated at 25%.

A dosage-dependent induction of luciferase activity was observed for both constructs. When the values of p(2x)$^3$E2BS-luciferase were normalized to the values of pGL2-promoter (no E2BSs), the relative induction seen by transfecting 7.5 μg and 15.0 μg of reporter DNA were similar at 3.9- and 3.5-fold, respectively. Transfection of 25.0 μg of reporter DNA resulted in a 6.5-fold relative induction of luciferase. The data suggest that physiological levels of E2 proteins are able to activate transcription from a construct containing E2BSs, and that the E2BS-luciferase assay system is useful to detect physiological levels of E2 proteins in cells. This supports the hypothesis that detection of E2 expression can be used to develop an in vitro assay for HPV infection of monolayer cultures. Recent reports indicate that E2BSs act with stronger cooperativity when placed in a context that allows DNA bending, such as in the p2x2xE2BS-lucif construct. (Berg and Steniund, 1997; Kovelman et al., 1996; Moskaluk and Bastia, 1987).

Transactivation of E2BS-luciferase constructs in CRPV-infected SCC-13 cells

To determine whether newly infected cells would express sufficient quantities of E2 proteins to specifically activate the E2BS-luciferase reporter assay, SCC-13 cells were infected with CRPV. CRPV was chosen initially for the following reasons: (i) a stock of CRPV virions produced in the xenograft system was available; (ii) this stock was shown to contain high numbers of virus particles; and (iii) the stock was shown to infect monolayer cell cultures wherein CRPV transcripts were detectable by Northern blot analyses as early as 17 h post infection. (Angell et al., 1992)

Figure 5:
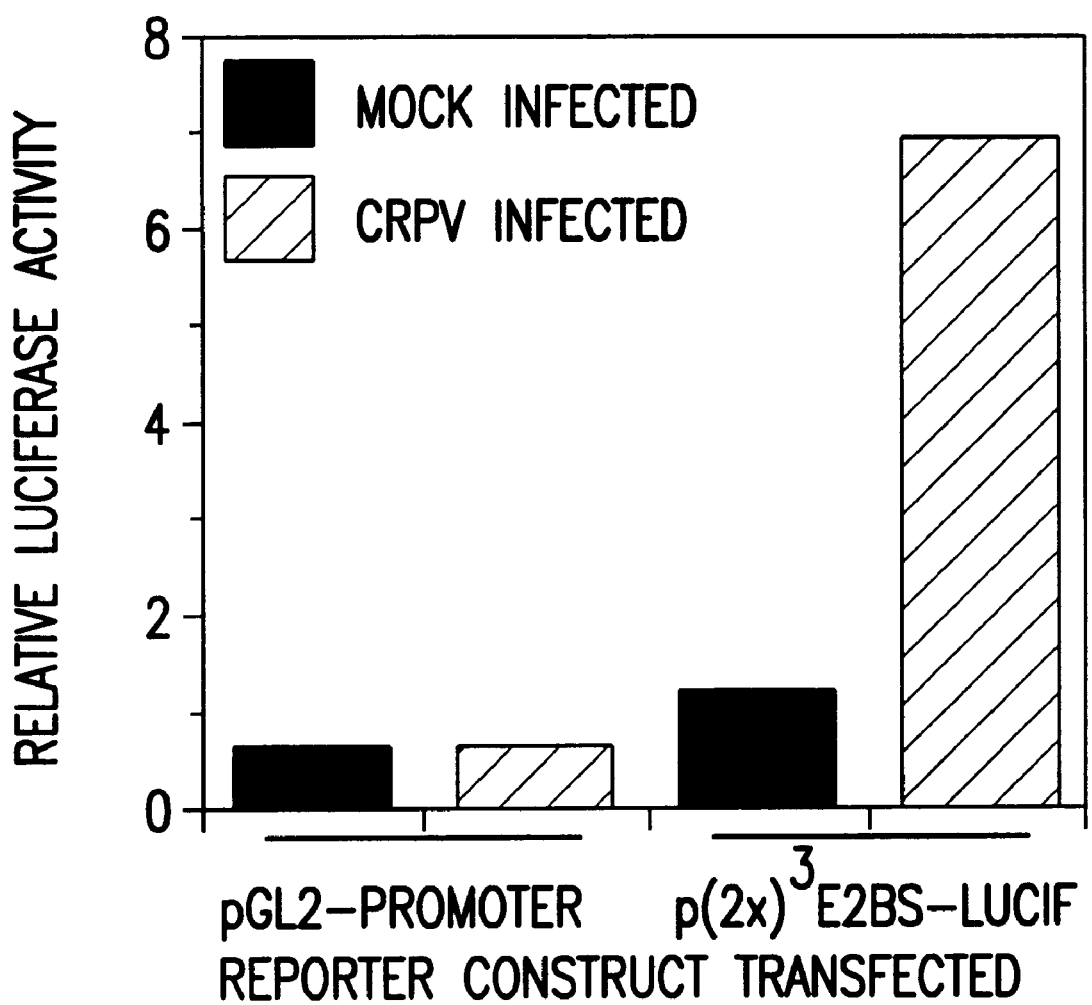
FIG. 5 shows transactivation of E2BS-reporter constructs in CRPV-infected SCC-13 cells.

SCC-13 cells were electroporated with 15 μg of either pGL2-promoter or p(2x)$^3$EBS-lucif as described in FIG. 4. SCC-13 cells were also electroporated with 15 μg of pCMVβ as a control for efficiency. The transfected cells were plated into 6-well tissue culture plates containing mitomycin C-treated fibroblast feeders and allowed to attach for 8 h; the wells appeared to be about 70% confluent. Using the infection information obtained by Angell and coworkers as a guide (1992), duplicate wells of cells were either mock infected or infected with a 100-μl inoculum of purified CRPV in a total volume of 1 ml of cell culture medium. At 15 h p.i., 1 ml of cell culture medium was added to each well. At 68 h p.i. (76 h p.t.) the cells were lysed and assayed for luciferase activity; the pCMVβ-transfected cells (mock-infected) were stained for β-galactosidase activity. FIG. 5 shows relative luciferase activity in cells transfected with either 15 μg of pGL2-promoter or p(2x)$^3$EBS-lucif. Transfected cells were either mock-infected (stippled bars) or CRPV-infected (striped bars). Values represent the averages of three counts each of duplicate assays performed in 6-well tissue culture dishes. The transfection efficiency in SCC-13 cells electroporated with pCMVβ by assaying for β-galactosidase activity was estimated at 50%.

The data showed that there was no difference in expression of luciferase in the SCC-13 cells containing the pGL2-promoter construct whether they were mock- or CRPV-infected (FIG. 5). This demonstrates that infection with CRPV does not nonspecifically activate the minimal SV40 promoter driving expression of luciferase. However, the CRPV-infected SCC-13 cells containing p(2x)$^3$E2BS-lucif had 5-fold greater expression of luciferase compared to their mock-infected counterparts. Staining for β-galactosidase activity in pCMVβ transfected SCC-13 cells indicated the transfection efficiency to be ≈50%. A number of conclusions can be drawn from these data. First, the human SCC-13 cell line is susceptible to the initial stages of infection by CRPV. This supports the idea that host range and tropism are determined at a stage following the attachment, penetration, uncoating, and expression of the first early vital genes, specifically E2. Second, CRPV infection specifically induces expression of luciferase dependent upon the consensus E2BSs. This indicates that the system is functional for defining the appropriate infection conditions of potentially any PV for which viral stocks are available. Third, the ability to use this transient assay suggests stable transfection of the E2BS-reporter gene is not required for such investigations.

Creation of E2BS-β-galactosidase (β-gal) constructs

Cells expressing the β-gal gene were fixed and directly stained for β-gal activity (MacGregor and Caskey, 1989).

Thus, E2-dependent expression of β-gal served as a direct quantitative assay for determining the extent of cellular infection. Because monolayer cells do not support the complete viral life cycle, there will be no spread of the virus after initial infection. As a result, individual cells staining blue were indicative of E2 expression resulting from HPV infection. This assay allows direct calculation of total cell percentages infected and of particle-to-infectious-unit ratios, an in vitro assay never before reported for HPVs.

E2BS-containing β-gal plasmids were constructed. Briefly, the β-gal protein coding sequences from pCMV (MacGregor and Caskey, 1989) were excised and cloned into each of the luciferase constructs. The resulting β-gal constructs are similar to the luciferase constructs except that the SV40 minimal promoter drives expression of β-gal.

DOCUMENTS CITED:

Androphy, E. J., D. R. Lowy and J. T. Schiller. *Nature* (London), 325:70–73, 1987.
Angell, M. G., N. D. Christensen and J. W. Kreider. *J. Virol. Meth.*, 39:207–216, 1992.
Berg, M. and A. Steniund. *J. Virol.*, 71:3853–3863, 1997.
Bouvard, V., A. Storey, D. Pim and L. Banks. *EMBO J.*, 13:5451–5459, 1994.
Broker, T. R. and M. Botchan. *Cancer Cells*, 4:17–36, 1986.
Bouma, S. P., Joseph, J. L., Marshall, R. L. and Laffler, T. G., U.S. Pat. No. 5,484,699, 1996.
Butel, J. S. *J. Natl. Cancer Inst.*, 48:285–299, 1972.
Christensen, N. D. and J. W. Kreider. *J. Virol.*, 64:3151–3156, 1990.
Del Vecchio, A. M., H. Romanczuk, P. M. Howley and C. C. Baker. *J. Virol.*, 66:5949–5958, 1992.
Dvoretzky, I., R. Shober, S. K. Chattopadhyay and D. R. Lowy. *Virol*, 103:369–375, 1980.
Garrido-Guerrero, E., Carrillo, E., Guido, M., Zamorano, R., Garcia-Carranca, A., Gariglia, P. *J. Virol.* 69(2):1319–1323, 1995.
Hawley-Nelson, P., et al., *EMBO J.* 7:525–531, 1988.
Herzog, A., Cravodor, A., Howard, S., Ballen, A., U.S. Pat. No. 4,983,728, 1991.
Hirochika, H., T. R. Broker and L. T. Chow. *J. Virol.*, 61:2599–2606, 1987.
Howley, P. M. *In: Fields Virology*, Third Edition. (Ed. B. N. Fields and D. M. Knipe) Raven Press, New York. pp. 2045–2076, 1996.
Kovelman, R., G. K. Bitter, E. Glezer, A. Y. Tsou and M. S. Barbosa. *J. Virol.*, 70:7549–7560, 1996.
Lambert, P. F. *J. Virol.*, 65:3417–3420, 1991.
Lancaster, W. D. and W. Meinke. *Nature* (London), 256:434–436, 1975.
Lancaster, W. D. and C. Olson. *Microbiol. Rev.*, 46:191–207, 1982.
MacGregor, G. R. and C. T. Caskey. *Nuc. Acids Res.*, 17:2365, 1989.
MacGregor, G. R. and C. T. Caskey. *In: Methods in Molecular Biology*. (Ed. E. J. Murray) The Humana Press Inc., Clifton, N.J. pp. 217–235, 1991.
Meijer, C. L., van den Brule, A. J., Walboomers, J. M., and Snipers, P. J., U.S. Pat. No. 5,364,758 1994.
Meyers, C., T. J. Mayer and M. A. Ozbun. *J. Virol.*, 71:7381–7386, 1997.
Moskaluk, C. and D. Bastia. Proc. Natl. Acad. Sci. USA, 85:1826–1830, 1987.
Myers, G., C. Baker, C. Wheeler, A. Halpern, A. McBride and J. Doorbar. (Ed.) Human papillomaviruses 1996. Los Alamos National Laboratory, Los Alamos, New Mexico, 1996.
Pfister, H. Obstet Gynecol. *Clin. North Am.*, 14:349–361, 1987.
Pfister, H. Rev. Physiol. Biochem. *Pharmacol*, 99:111–181, 1984.
Rheinwald, J. G. and M. A. Beckett. *Cancer Res.*, 41:1657–1663, 1981.
Roizman, B. *In: Virology*, Second Edition. (Ed. B. N. Fields, D. M. Knipe and et al.) Raven Press, New York. pp. 87–94, 1990.
Rowson, K. E. K. and B. W. J. Mahy. *Bateriol. Rev.*, 31:110–131, 1967.
Smith, L. H., C. Foster, H. E. Hitchcock and R. Isseroff. *Journal of Investigative Dermatology*, 10 1:292–295, 1993.
Smith, L. H., C. Foster, H. E. Hitchcock, G. S. Leiserowitz, K. Hall, R. Isseroff, N. D. Christensen and J. W. Kreider. *Journal of Investigative Dermatology*, 105:438–444, 1995.
Spalholz, B. A., J. C. Byrne and P. M. Howley. *J. Virol.*, 62:3143–3150, 1988.
Steinberg, B. M., K. J. Auborn, J. L. Brandsma and L. B. Taichman. *J. Virol.*, 63:957–960, 1989.
Thierry, F., N. Dostatni, F. Amos and M. Yaniv. *Mol Cell. Biol.*, 10:4431–4437, 1990.
Thierry, F. and M. Yaniv. *EMBO J.*, 6:3391–3397, 1987.
Ushikai, M., M. J. Lace, Y. Yamakawa, M. Kono, J. Anson, T. lshiji, S. Parkkinen, N. Wicker, M.-E. Valentine, 1. Davidson, L. P. Turek and T. H. Haugen. *J. Virol.*, 68:6655–6666, 1994.
Ustav, M. and A. Stenlund. *EMBO J.*, 10:449–457, 1991.
Wasylyk, B., Wasylyk, C. and Chambon, P. *Fed. Proc.*, 43(2):226–234, 1984.
Zhou, J., L. Gissmann, H. Zentgraf, H. Muller, M. Picken and M. Muller. *Virology*, 214:167–176, 1995.
zur Hausen, H. and A. Schneider. In: The Papovaviridae. vol. 2. The papillomaviruses. (Ed. N. P. Salzman and P. M. Howley) Plenum Press, New York, N.Y. pp.245–263, 1987.

We claim:

1. A method of titering papillomaviruses or determining the susceptibility of a cell to a papillomavirus, said method comprising:
   (a) obtaining a population of cells comprising an expression vector comprising at least one E2-binding site and a reporter gene operably linked to a promoter;
   (b) contacting the population of cells with papillomavirus; and
   (c) quantifying expression of the reporter gene from which the quantity of the papillomaviruses is inferred, or the susceptibility of a cell to the papillomavirus is inferred.

2. The method of claim 1, wherein the population of cells are susceptible and permissive to papillomavirus.

3. The method of claim 2, wherein the population of cells is an immortalized epithelial cell line.

4. The method of claim 3, wherein the epithelial cell line is a keratinocyte line.

5. The method of claim 4, wherein the keratinocyte cell line is a human cell line.

6. The method of claim 5, wherein the human keratinocyte cell line is SCC-13.

7. A kit for titering a papillomavirus or determining the susceptibility of a cell to a papillomavirus, said kit comprising:
   (a) a cell comprising an expression vector comprising at least one E2-binding site and a reporter gene operably linked to a promoter; and
   (b) reagents for detecting the expression of the reporter gene.

* * * * *

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: E2BS
<220> FEATURE:
```

-continued

```
<223> OTHER INFORMATION: "n" bases may be A, T, C or G

<400> SEQUENCE: 1
accgnnnncg gt                                                                12

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
caccgaaaac ggttcaaccg aaaacggttg tac                                         33

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
atccaccgaa aacggttcaa ccgaaaacgg tta                                         33

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: E2BS

<400> SEQUENCE: 4
accgaaaacg gt                                                                12
```